(12) United States Patent
Ohmiya et al.

(10) Patent No.: US 9,446,402 B2
(45) Date of Patent: Sep. 20, 2016

(54) SPECIMEN SUPPLYING TOOL AND SPECIMEN ANALYSING INSTRUMENT USING THE SAME

(75) Inventors: Kazuhiro Ohmiya, Kyoto (JP); Kaori Ishizaki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 244 days.

(21) Appl. No.: 12/530,146

(22) PCT Filed: Jul. 17, 2008

(86) PCT No.: PCT/JP2008/062909
§ 371 (c)(1),
(2), (4) Date: Sep. 4, 2009

(87) PCT Pub. No.: WO2009/014060
PCT Pub. Date: Jan. 29, 2009

(65) Prior Publication Data
US 2010/0054992 A1    Mar. 4, 2010

(30) Foreign Application Priority Data
Jul. 20, 2007    (JP) .................................. 2007-189429

(51) Int. Cl.
*G01N 31/00*    (2006.01)
*B01L 3/02*    (2006.01)
(Continued)

(52) U.S. Cl.
CPC ............ *B01L 3/0262* (2013.01); *B01L 3/0293* (2013.01); *G01N 35/1016* (2013.01); *B01L 3/5088* (2013.01); *B01L 2300/0819* (2013.01); *G01N 2035/1034* (2013.01)

(58) Field of Classification Search
CPC ........... B01L 3/502746; B01L 3/5027; B01L 3/502; G01N 35/085
See application file for complete search history.

(56) References Cited

U.S. PATENT DOCUMENTS 4,693,834 A * 9/1987 Hossom ...................... 210/767
4,818,677 A * 4/1989 Hay-Kaufman et al. ......... 435/4
(Continued)

FOREIGN PATENT DOCUMENTS

CN    1720101    1/2006    ............... B01J 19/00
EP    1 398 614    3/2004    ............... G01N 1/34
(Continued)

OTHER PUBLICATIONS

Office Action dated Mar. 3, 2011 in corresponding Chinese Patent Application No. 200880000858.0 (partial translation included).
(Continued)

*Primary Examiner* — Jill Warden
*Assistant Examiner* — Brittany Fisher
(74) *Attorney, Agent, or Firm* — Morgan, Lewis & Bockius LLP (57) ABSTRACT

A specimen supplying tool in which structure is simple, and a liquid specimen and air bubbles do not remain within a through-bore for introduction of a specimen, is provided. The specimen supplying tool includes a substrate 11 and a through-bore 13 provided in the substrate 11. One opening of the through-bore 13 is a specimen inflow port, and the other opening of the through-bore 13 is a specimen outflow port. The specimen supplying tool further includes a projection portion 14 projecting from a part p of a marginal part of the specimen outflow port. A liquid specimen is introduced from the specimen inflow port to the through-bore 13. When the introduced liquid specimen is discharged from the specimen outflow port, and supplied to a specimen analyzing instrument, the liquid specimen is drawn to the projection portion 14, led by the projection portion 14, and supplied to the specimen analyzing instrument.

4 Claims, 6 Drawing Sheets

(51) Int. Cl.
*G01N 35/10* (2006.01)
*B01L 3/00* (2006.01)

(56) References Cited

U.S. PATENT DOCUMENTS

| | | | | |
|---|---|---|---|---|
| 4,981,786 | A * | 1/1991 | Dafforn et al. | 435/7.92 |
| 5,948,695 | A * | 9/1999 | Douglas et al. | 436/518 |
| 6,719,887 | B2 | 4/2004 | Hasegawa et al. | |
| 7,517,499 | B2 | 4/2009 | Kahl | |
| 2002/0092767 | A1 | 7/2002 | Bjornson | |
| 2005/0019231 | A1 | 1/2005 | Kahl | 422/187 |
| 2007/0004029 | A1 | 1/2007 | Aoyagi | |
| 2007/0102362 | A1 | 5/2007 | Iida et al. | |

FOREIGN PATENT DOCUMENTS

| | | | |
|---|---|---|---|
| EP | 1 588 764 | 10/2005 | B01L 3/00 |
| JP | 2001-517789 A | 10/2001 | |
| JP | 2002-196001 | 7/2002 | |
| JP | 2002-202283 | 7/2002 | |
| JP | 2005-504317 | 2/2005 | |
| JP | 2005-265685 | 9/2005 | |
| JP | 2006-349347 | 12/2006 | |
| JP | 2007-040969 | 2/2007 | |
| WO | 99/15876 A | 4/1999 | |
| WO | WO 02/080822 | 10/2002 | A61F 2/44 |
| WO | WO 2004/050246 | 6/2004 | B01L 3/00 |
| WO | 2005/022169 | 3/2005 | |

OTHER PUBLICATIONS

Extended European Search Report dated Mar. 8, 2011 in corresponding European Patent Application No. EP 08 791 263.0.

* cited by examiner

SPECIMEN SUPPLYING TOOL AND SPECIMEN ANALYSING INSTRUMENT USING THE SAME

TECHNICAL FIELD

The present invention relates to a specimen supplying tool and a specimen analyzing instrument.

BACKGROUND ART

Figure 13:
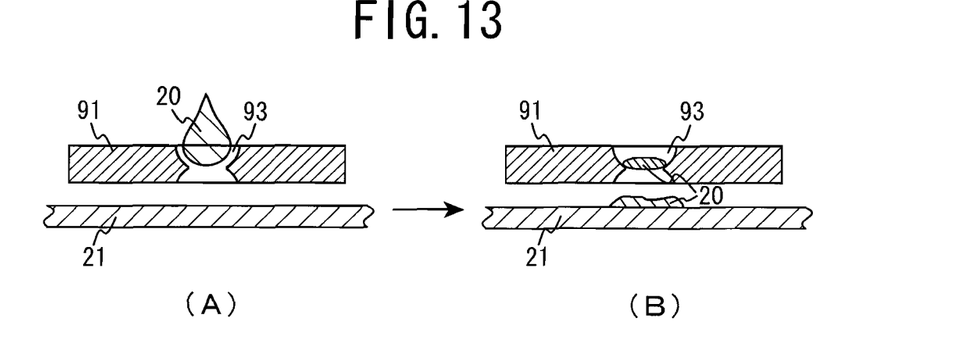
FIG. 13 is a cross-section view showing one example of a conventional specimen supplying portion.

Conventionally, with respect to biochemical examinations, clinical examinations, and the like, specimen analyzing instruments are used widely. In the specimen analyzing instruments, a liquid specimen is supplied from a specimen supplying portion. The schematic cross-section view in FIG. 13 (A) shows a specimen supplying portion of a conventional specimen analyzing instrument. As shown in FIG. 13 (A), this specimen supplying portion includes a substrate 91 and a through-bore 93 provided in the substrate 91. One opening of the through-bore 93 (upper opening in FIG. 13 (A)) is a specimen inflow port, and the other opening of the through-bore 93 (lower opening in FIG. 13 (A)) is a specimen outflow port. In this specimen supplying portion, a liquid specimen 20 is introduced from the specimen inflow port to the through-bore 93. The introduced liquid specimen 20 is discharged from the specimen outflow port, and supplied to a specimen developing layer 21 of the specimen analyzing instrument. The specimen developing layer is formed from porous component such as a filter paper, and the like and the liquid specimen develops in the specimen developing layer, and contacts with a reagent that is arranged at the downstream side. Further, the component of the liquid specimen reacts with the reagent and a chromogenic reaction or a color change occurs. The chromogenic reaction or the color change is observed with visual contact, or is measured with an optical device such as a spectrophotometer, and the like.

Figure 14:
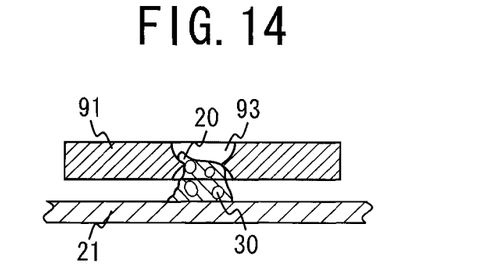
FIG. 14 is a cross-section view showing one example of a conventional specimen supplying portion.

A cross-section shape of the through-bore 93 of the specimen supplying portion is a so called a hourglass-shape in which the bore diameter decreases as going to the direction of thickness from the specimen inflow port to the middle of the direction of thickness of the substrate 91, and the bore diameter increases as going to the direction of thickness from the middle of the direction of thickness of the substrate 91 to the specimen outflow port. In addition, a cross-section shape of a through-bore of a specimen supplying portion includes a bowl-shape (approximate hemispherical shape), and the like. However, with respect to a conventional specimen supplying portion, as shown in FIG. 13 (B), there is a case that a liquid film is generated on the liquid specimen 20 within the through-bore 93, and some of the liquid specimen 20 remains within the through-bore 93. Further, when the liquid specimen 20 is introduced to the through-bore 93 by using a pipette, and the like, as shown in FIG. 14, there is a case that an air bubble 30 is generated within the liquid specimen 20. In the conventional specimen supplying portion, there is a case that there is no space for the generated air bubble 30 in the liquid specimen 20 to escape, and some of the liquid specimen 20 remains within the through-bore 93 by the effect of this air bubble 30. In this way, when some of the liquid specimen 20 remains within the through-bore 93, it adversely affects analysis of the liquid specimen 20.

On the other hand, a specimen analyzing instrument provided with a means for removing generated air bubbles in a liquid specimen, such as using a filter, and the like, is proposed (ref. patent documents 1 and 2). However, to take means such as using the filter, and the like for solving the problem of remaining a liquid specimen makes the structure of a specimen analyzing instrument complicated, and as a result, manufacturing becomes cumbersome and complicated, and also expensive.

Patent document 1: JP 2002-196001 A
Patent document 2: JP 2002-202283 A

DISCLOSURE OF INVENTION

Hence, the present invention is intended to provide a specimen supplying tool in which the structure is simple and a liquid specimen and air bubbles do not remain within a through-bore for introducing a specimen, and a specimen analyzing instrument using the same.

In order to achieve the aforementioned object, the specimen supplying tool of the present invention is a specimen supplying tool used for supplying a liquid specimen to a specimen analyzing instrument, the specimen supplying tool of the present invention includes a substrate and a through-bore provided in the substrate, the through-bore includes a specimen inflow port and a specimen outflow port, the specimen inflow port is one opening of the through-bore, the specimen outflow port is the other opening of the through-bore, the specimen supplying tool further includes a projection portion projecting from a marginal part of the specimen outflow port toward the direction of movement of the specimen, and when the liquid specimen is introduced from the specimen inflow port to the through-bore, and the introduced liquid specimen is discharged from the specimen outflow port and supplied to the specimen analyzing instrument, the liquid specimen is gravitated to the projection portion, led by the projection portion, and supplied to the specimen analyzing instrument.

The specimen analyzing instrument of the present invention includes a specimen supplying portion and a specimen analyzing portion. The specimen supplying portion is composed of the specimen supplying tool of the present invention.

The specimen supplying tool of the present invention has a projection portion projecting from a marginal part of the specimen outflow port toward the direction of movement of the specimen. Therefore, with respect to the specimen supplying tool of the present invention, a liquid specimen is gravitated to the projection portion, led by the projection portion, and supplied to a specimen analyzing instrument. As a result, with respect to the specimen supplying tool of the present invention, a liquid specimen does not remain within a through-bore for introducing a specimen, and also air bubbles do not remain therein. Furthermore, the structure of the projection portion can be simple, and with the result that manufacturing of a specimen supplying tool and a specimen analyzing instrument is achieved with ease and at low cost according to the present invention.

DESCRIPTION OF THE INVENTION

With respect to the present invention, "liquid specimen" is a flowable specimen, for example, such as liquid, emulsion, suspension, and the like. The liquid specimen is not particularly limited, and examples thereof include whole blood, serum, plasma, saliva, urine, spinal fluid, and the like. In addition, the liquid specimen may be a specimen in which a solid object to be analyzed is dissolved or dispersed in liquid such as buffer, and the like.

With respect to the specimen supplying tool of the present invention, the projection portion may project from a part of a marginal part of the specimen outflow port toward the direction of movement of the specimen.

With respect to the specimen supplying tool of the present invention, the projection portion may project from the whole marginal part of the specimen outflow port toward the direction of movement of the specimen, a circumferential height at a marginal part on the side opposite to the specimen outflow port side of the projection portion is uneven, and when the liquid specimen may be introduced from the specimen inflow port to the through-bore, and the introduced liquid specimen is discharged from the specimen outflow port, and supplied to the specimen analyzing instrument, the liquid specimen may be drawn to the longest part of the projection portion, may be led by the longest part of the projection portion, and may be supplied to the specimen analyzing instrument.

With respect to the specimen supplying tool of the present invention, preferably, a specimen analyzing instrument is a specimen analyzing instrument in which a liquid specimen moves from upstream to downstream, the projection portion is formed on the upstream side of a marginal part of the specimen outflow port, and the projection portion is not formed on the downstream side of a marginal part of the specimen outflow port. In this sort of form, retention of a liquid specimen and air bubbles further can be prevented.

With respect to the specimen supplying tool of the present invention, with consideration of ease of introduction of the liquid specimen, a bore diameter of the specimen inflow port is preferably longer than a bore diameter of the specimen outflow port.

With respect to the specimen supplying tool of the present invention, a bore diameter of the through-bore may decrease in the direction of thickness from the specimen inflow port to the middle of the thickness direction of the substrate, and a bore diameter may increase in the thickness direction from the middle of the direction of thickness of the substrate to the specimen outflow port.

With respect to the specimen analyzing instrument of the present invention, preferably, the specimen analyzing instrument further includes a specimen developing layer, the specimen supplying portion is formed on the upstream side of the specimen developing layer, the specimen analyzing portion is formed on the downstream side of the specimen developing layer, and the liquid specimen discharged from the specimen outflow port of the specimen supplying portion is supplied to the specimen analyzing portion of the specimen developing layer.

With respect to the specimen analyzing instrument of the present invention, the specimen analyzing instrument may further include a developing solvent supplying portion on the specimen developing layer upstream side than the specimen supplying portion, and the liquid specimen may develop in the specimen developing layer by the developing solvent supplied from the developing solvent supplying portion.

The specimen analyzing instrument of the present invention may include an observation port for observing the specimen analyzing portion from the outside.

Next, the specimen supplying tool of the present invention is described by examples. However, the present invention is not limited to the following examples.

Example 1

Figure 1:
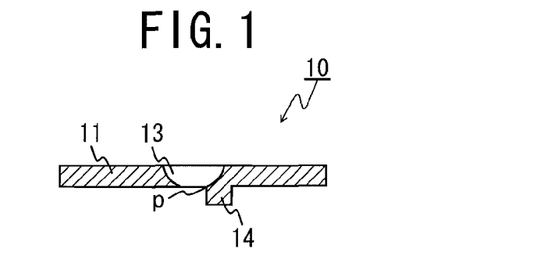
FIG. 1 is a cross-section view showing one example of a specimen supplying tool of the present invention.

The cross-section view in FIG. 1 shows one example of the specimen supplying tool of the present invention. As shown in FIG. 1, this specimen supplying tool 10 includes a substrate 11 and a through-bore 13 provided in the substrate 11. One opening of the through-bore 13 (upper opening in FIG. 1) is a specimen inflow port, and the other opening of the through-bore 13 is a specimen outflow port. This specimen supplying tool 10 further includes a projection portion 14 projecting from a part of a marginal part of the specimen outflow port (point p in FIG. 1) in the direction of movement of a specimen.

A size of the substrate 11 is not particularly limited, and is, for example, in the range of 5 to 200 mm in length, in the range of 1 to 50 mm in width, and in the range of 0.1 to 20 mm in thickness.

A material of the substrate 11 is not particularly limited, and examples thereof include polyethylene terephthalate (PET), polystyrene, polyester, cellulose acetate, and the like.

A shape of the specimen inflow port is not particularly limited as long as it does not adversely affect the introduction of the liquid specimen. In addition, a shape of the specimen outflow port also is not particularly limited as long as it does not adversely affect the discharge of the liquid specimen. Examples of shapes of the specimen inflow port and the specimen outflow port include circle, ellipse, polygonal shape (for example, rectangle), and the like.

The bore diameter of the specimen inflow port and the bore diameter of the specimen outflow port are, for example, in the range of 0.5 to 500 mm, preferably in the range of 1.0 to 200 mm, and more preferably in the range of 1.5 to 20 mm. As described above, the bore diameter of the specimen inflow port is preferably longer than the bore diameter of the specimen outflow port. When shapes of the specimen inflow port and the specimen outflow port are circular, a shape of the through-bore may be a bowl-shape shown in FIG. 1 (approximate hemispherical shape), or may be a funnel shape, for example.

Figure 2:
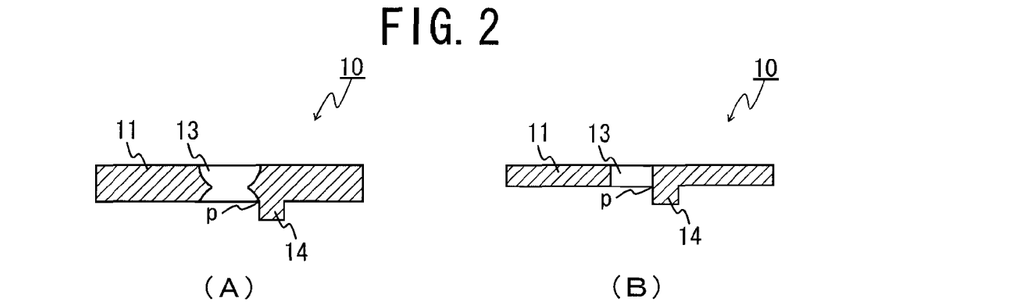
FIG. 2 is a cross-section view showing another example of a specimen supplying tool of the present invention.

As described above, the bore diameter of the through-bore may decrease in the direction of thickness from the specimen inflow port to the middle of the direction of thickness of the substrate, and the bore diameter may increase in the direction of thickness from the middle of the direction of the substrate to the specimen outflow port. In this case, when shapes of the specimen inflow port and the specimen outflow port are circular, the through-bore is an hourglass-shape shown in FIG. 2 (A). Further, as shown in FIG. 2 (B), with respect to the through-bore 13, the bore diameter of the specimen inflow port and the bore diameter of the specimen outflow port may be the same. In addition, in FIGS. 2 (A) and (B), identical parts to those shown in FIG. 1 are indicated with identical numerals and symbols.

Figure 3:
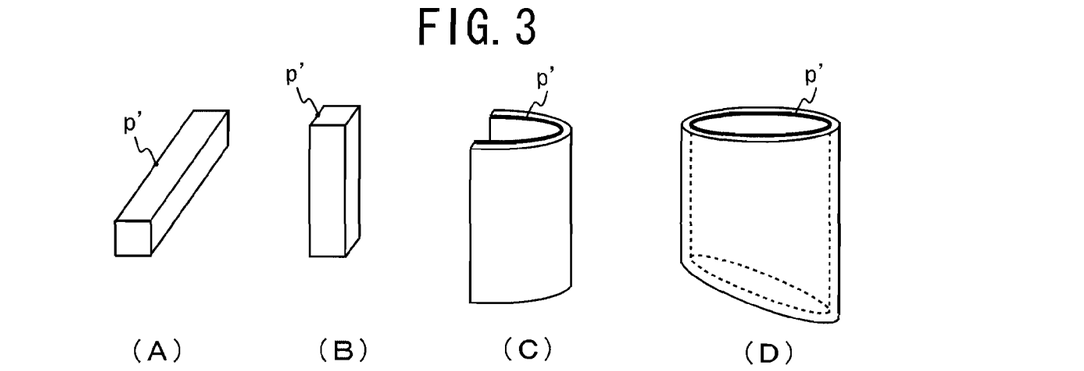
FIG. 3 shows examples of a projection portion of the present invention.

As described above, the projection portion 14 is projecting from a part of the specimen outflow port in the direction of the movement of the specimen. FIGS. 3 (A), (B), and (C) show examples of the shapes of the projection portion. The projection portion shown in FIG. 3 (A) is a rectangular parallelepiped shape extending horizontally. When this projection portion is used in the specimen supplying tool 10 shown in FIG. 1, the point p' shown in FIG. 3 (A) contacts with the point p shown in FIG. 1 (a part of a marginal part of the specimen outflow port). The projection portion shown in FIG. 3 (B) is a rectangular parallelepiped shape extending vertically. When this projection portion is used in the specimen supplying tool 10 shown in FIG. 1, the point p' shown in FIG. 3 (B) contacts with the point p shown in FIG. 1 (a part of a marginal part of the specimen outflow port). When a shape of the specimen outflow port is, for example, circle, the projection portion may be, for example, a half-cylindrical shape such as shown in FIG. 3 (C). The projection portion shown in FIG. 3 (C) contacts with a part (half) of a marginal part of the specimen outflow port at the arc p'. Shapes of the projection portion are not limited to these examples. The projection portion may be any shape as long as it projects from a part of the specimen outflow port. The liquid specimen introduced to the through-bore is, for example, drawn to the projection portion and led by the projection portion by surface tension, gravity, and the like, and supplied to the specimen analyzing instrument.

The projection portion may project from the whole marginal part of the specimen outflow port toward the direction of movement of the specimen. In this case, circumferential height at a marginal part on the side opposite to the specimen outflow port side of the projection portion is uneven. FIG. 3 (D) shows one example of a shape of the projection portion in this case. This example is one example in a case where a shape of the specimen outflow port is circular. The shape of the projection portion shown in FIG. 3 (D) is a shape in which a circular cylinder is cut at an angle, and a circumferential height at a marginal part on the side opposite (lower side in FIG. 3 (D)) to the specimen outflow port side (the upper side in FIG. 3 (D)) is uneven. The projection portion shown in FIG. 3 (D) contacts with the whole specimen outflow port at the circle p'. A shape of the projection portion in this case also is not limited to this example, and may be any shape as long as a circumferential height at a marginal part on the side opposite to the specimen outflow port side is uneven. In this case, the liquid specimen introduced to the through-bore is drawn to the longest part of the projection portion (lower right part of the projection portion shown in FIG. 3 (D)), led by the longest part of the projection portion, and supplied to the specimen analyzing instrument.

A size of the projection portion can be decided suitably according to the bore diameter of the specimen outflow port, and the like, and is not particularly limited. The maximum length of the projection portion (length from a marginal part of the specimen outflow port to the farthest portion on the lower side) is, for example, in the range of 0.1 to 20 mm, preferably in the range of 0.5 to 10 mm, more preferably in the range of 1 to 5 mm.

Figure 4:
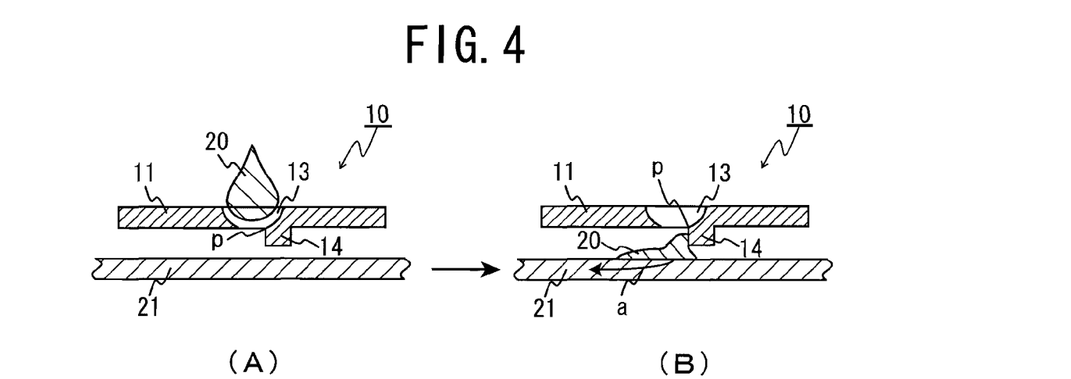
FIG. 4 is a cross-section view for explaining a mechanism of supply of a specimen with respect to one example of a specimen supplying tool of the present invention.

Next, with reference to FIG. 4, with respect to the specimen supplying tool of the present invention, a mechanism of liquid specimen supply is described, taking the case using the specimen supplying tool 10 shown in FIG. 1 for an example.

First, as shown in FIG. 4 (A), a liquid specimen 20 is introduced from the specimen inflow port to the through-bore 13. The introduced liquid specimen 20 is, as shown in FIG. 4 (B), gravitated to the projection portion 14, led by the projection portion 14, and supplied to a specimen developing layer 21 of the specimen analyzing instrument. Therefore, with respect to the specimen supplying tool 10, the liquid specimen 20 does not remain within the through-bore 13, and air bubbles also do not remain therein. Further, the structure of the projection portion 14 is simple, and manufacturing of the specimen supplying tool 10 is achieved with ease and at low cost. The liquid specimen 20 supplied to the specimen developing layer 21, as shown by the arrow a in FIG. 4 (B), moves (develops) from upstream to downstream in the specimen developing layer 21. In addition, with respect to the specimen supplying tool of the present invention, "include a projection portion projecting from a part of a marginal part of the specimen outflow port toward the direction of movement of the specimen" means, for example, as shown in FIGS. 4 (A) and (B), that when the liquid specimen 20 is supplied to the specimen developing layer 21, the projection portion 14 is projecting from a part of a marginal part of the specimen outflow port (point p in FIG. 4) toward the specimen developing layer 21 side. The case of including a projection portion projecting from the whole marginal part of the specimen outflow port toward the direction of movement of the specimen which is not shown, is as well.

The projection portion 14 is preferred to be formed on the upstream side of a marginal part of the specimen outflow port, and is not formed on the downstream side of a marginal part of the specimen outflow port. This reason is described with reference to FIG. 5. In addition, in FIG. 5, identical parts to those shown in FIG. 4 are indicated with identical numerals and symbols.

Figure 5:
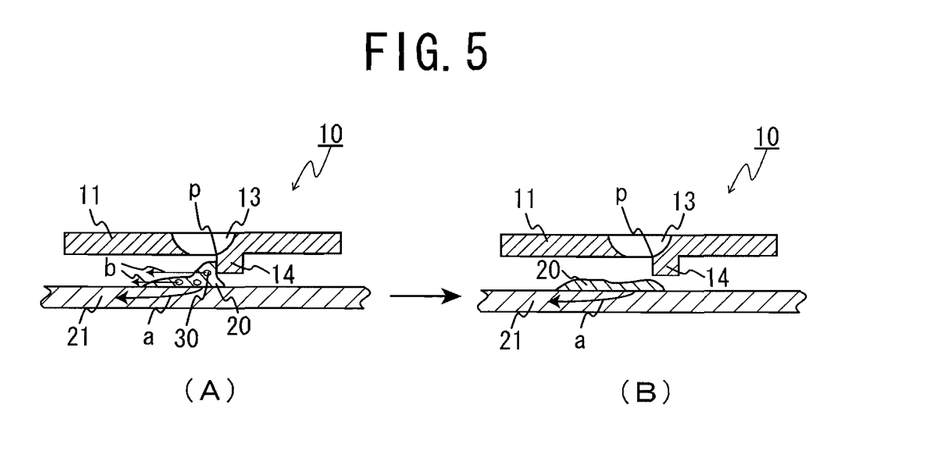
FIG. 5 is a cross-section view for explaining a flow of air bubbles with respect to one example of a specimen supplying tool of the present invention.

When the liquid specimen 20 is introduced to the through-bore 13 by using a pipette, and the like, as shown in FIG. 5 (A), there is a case in which air bubble 30 is generated in the liquid specimen 20. In this example, because the projection portion 14 is not formed on the downstream side of a marginal part of the specimen outflow port (left side in FIG. 5), even if air bubble 30 is generated in the liquid specimen 20, as shown by the arrow b, the air bubble 30 escapes to the space of the downstream side (left side in FIG. 5). As a result, with respect to the specimen supplying tool 10, as shown in FIG. 5 (B), the liquid specimen 20 more preferably can be supplied to the specimen developing layer 21.

Figure 6:
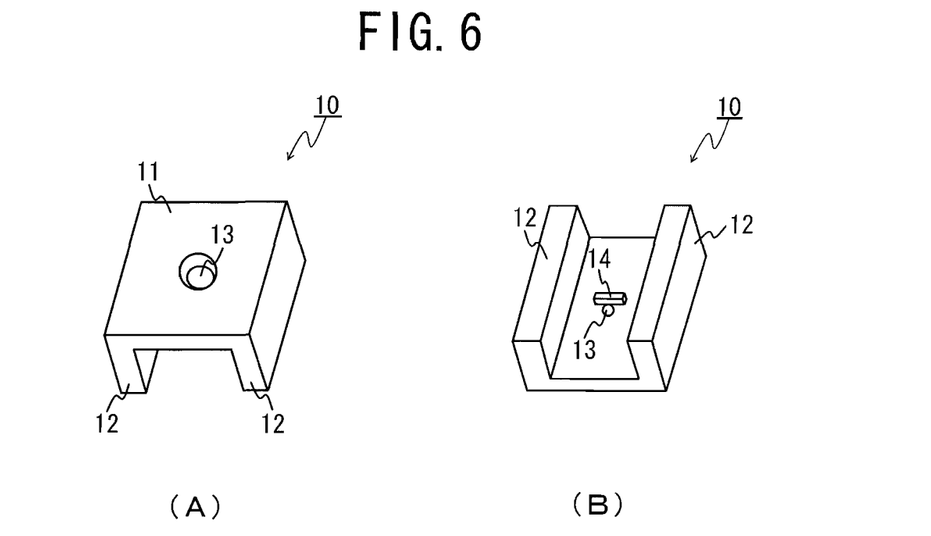
FIG. 6 is a perspective view showing yet another example of a specimen supplying tool of the present invention.

With respect to the specimen supplying tool of the present invention, the substrate further may include a sidewall. FIG. 6 shows an example of a specimen supplying tool of the present invention having the sidewalls. In FIG. 6, identical parts to those shown in FIG. 1 are indicated with identical numerals and symbols. FIG. 6 (A) is an overhead view of the specimen supplying tool 10, and FIG. 6 (B) is a view looked from underneath of the specimen supplying tool 10. As shown in FIG. 6, with respect to this specimen supplying tool 10, the substrate 11 further includes sidewalls 12 on each of the right and left end. Further, with respect to the specimen supplying tool 10, a projection portion 14 shaped as shown in FIG. 3 (A) is projecting from a part of a marginal part of the specimen outflow port. The length of the sidewalls 12 may be the same length as the substrate 11. The width of the sidewalls 12 is not particularly limited, and is, for example, in the range of 1 to 50 mm, preferably in the range of 5 to 40 mm, and more preferably in the range of 5 to 15 mm. The height of the sidewalls 12 (the downward height from the substrate 11) is not particularly limited as long as it is higher (longer) than the maximum length of the projection portion 14, for example, and is, for example, in the range of 0.1 to 20 mm, preferably in the range of 0.5 to 10 mm, and more preferably in the range of 2 to 8 mm.

Figure 7:
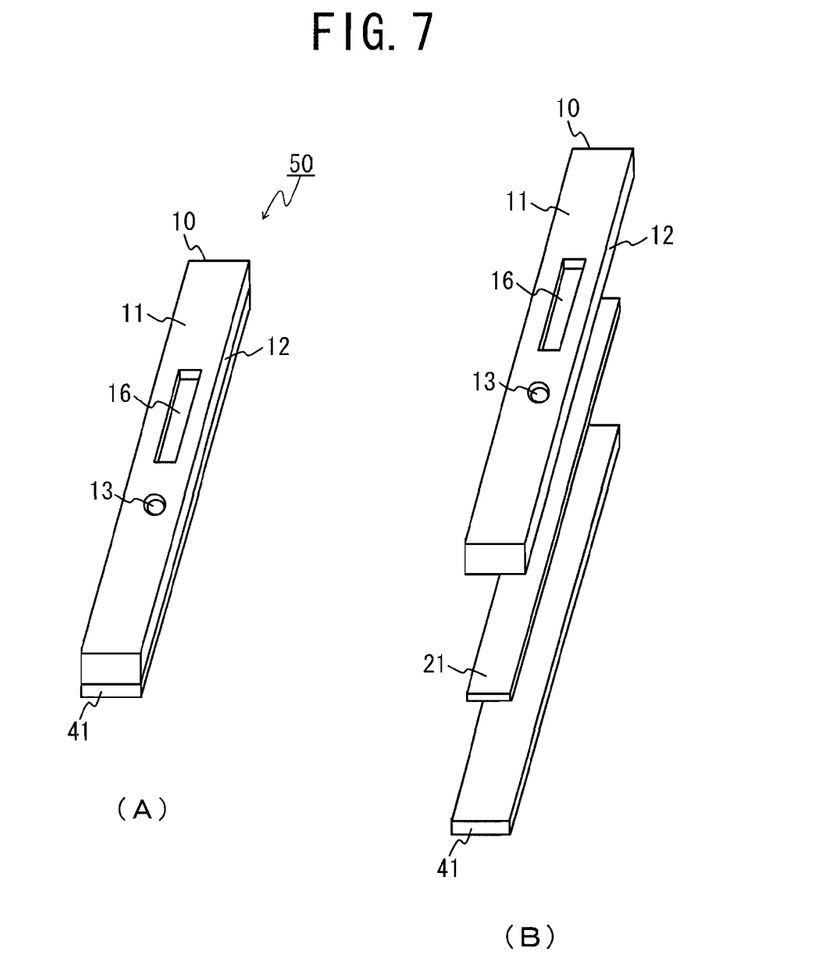
FIG. 7 is a perspective view showing configuration of one example of a specimen analyzing instrument of the present invention.

FIG. 7 shows one example of a specimen analyzing instrument using the specimen supplying tool of the present invention. In FIG. 7, identical parts to those shown in FIG. 1 are indicated with identical numerals and symbols. FIG. 7 (A) is a perspective view of the specimen analyzing instrument 50, and FIG. 7 (B) is an exploded view thereof. As shown in FIG. 7, this specimen analyzing instrument 50 has a cover member 10, a specimen developing layer 21, and a basal plate 41 as major configuration members. The cover member 10 includes the substrate 11, a through-bore 13 formed on the substrate 11, and the specimen supplying tool of the present invention. The cover member 10 has sidewalls 12 on all sides. The cover member 10 has an observation port 16 for observing a specimen analyzing portion of the specimen developing layer 21 from outside. With respect to the specimen analyzing instrument 50 of this example, the specimen supplying tool of the present invention is incorporated in the cover member 10 by casting. However, the present invention is not particularly limited to this. The specimen supplying tool of the present invention may be a separated independent member used as one part of the specimen analyzing instrument.

A size of the observation port 16 is not particularly limited, and is, for example, in the range of 2 to 100 mm in length, and is in the range of 2 to 50 mm in width.

A material forming the specimen developing layer 21 is not particularly limited as long as it supports capillary action, and for example, a cellulose membrane; a cellulose derivative membrane such as cellulose acetate, nitrocellulose, and the like; a porous film such as a glass filter, a filter paper, and the like, can be used. A size of the specimen developing layer 21 is not particularly limited, and for example, the length is in the range of 4.5 to 190 mm (in the range of 5 to 95% of the length of the substrate 11), the width is in the range of 0.95 to 47.5 mm (in the range of 5 to 95% of the width of the substrate 11), and the thickness is in the range of 0.025 to 0.25 mm.

A material of a basal plate 41 is not particularly limited, and examples thereof include a material is that the same as a material of the substrate 11. The length and width of the basal plate 41 are also same as the length and width of the substrate 11. The thickness of the basal plate 41 is not particularly limited, and is, for example, in the range of 0.005 to 0.5 mm.

Lamination of the specimen developing layer 21 over the basal plate 41 can be conducted by a common procedure, and for example, the specimen developing layer 21 simply is fixed on the basal plate 41 by using a double-sided tape or an adhesive agent.

An installation method of the cover member 10 over the basal plate 41 and the specimen developing layer 21 is not particularly limited. For example, when the cover member 10 has a projection portion for fixing and the basal plate 41 has an insertion port for the projection portion formed at a position corresponding to the projection portion, the cover member 10 can be fixed on the basal plate 41 and the specimen developing layer 21 by the projection portion and the insertion port. More than one projection portion and insertion port preferably are formed for fixing the cover member for certain.

Figure 8:
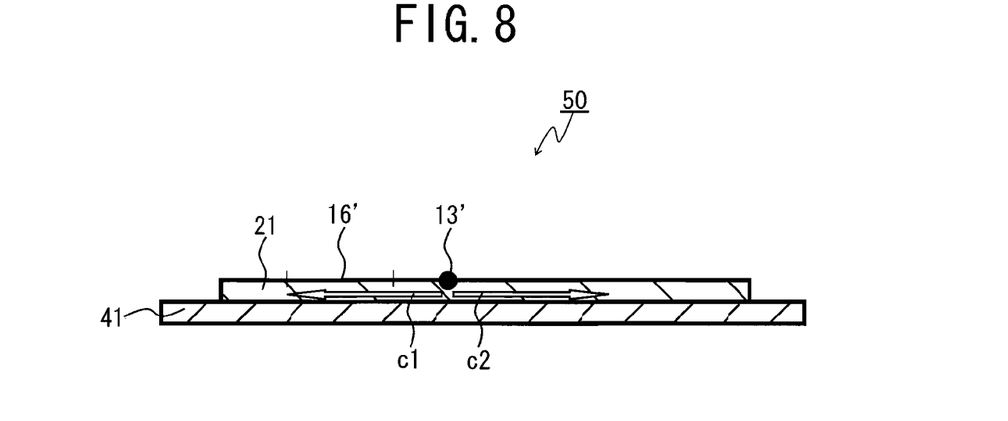
FIG. 8 is a cross-section view for explaining a flow of a specimen with respect to one example of a specimen analyzing instrument of the present invention.

Next, analysis of a liquid specimen using this specimen analyzing instrument 50 is explained with reference to FIG. 8. In addition, in FIG. 8, the cover member 10 is omitted as a matter of convenience.

First, a liquid specimen is introduced to the through-bore formed on the cover member. The introduced liquid specimen is supplied to a specimen supplying portion 13' in the specimen developing layer 21. In addition, the specimen supplying portion 13' is located under the through-bore formed on the cover member.

The liquid specimen supplied to the specimen supplying portion 13', as shown by the arrow c 1, develops to the downstream side of the specimen developing layer 21 (left side in FIG. 8), and reaches to a specimen analyzing portion 16' of the specimen developing layer 21. The specimen analyzing portion 16' is located under the observation port formed on the cover member. The liquid specimen supplied to the specimen supplying portion 13', as shown by the arrow c 2, further may develop opposite to the side of the specimen analyzing portion 16' side of the specimen developing layer 21 (right side in FIG. 8). However, when the specimen supplying portion 13' side is the upstream side, and the specimen analyzing portion 16' side is the downstream side, preferably the liquid specimen is led to the downstream side (the specimen analyzing portion 16' side) by forming the projection portion on the upstream side of a marginal part of the specimen outflow port, and not forming on the downstream side of a marginal part of the specimen outflow port.

A reagent is arranged in the specimen analyzing portion 16'. The reagent reacts with a target component to be analyzed in the liquid specimen and a chromogenic reaction or a color change occurs. Analysis of the liquid specimen can be conducted by observing the chromogenic reaction or the color change with visual contact, or by measuring the same with an optical device such as a spectrophotometer, and the like, from the observation port formed on the cover member.

Figure 9:
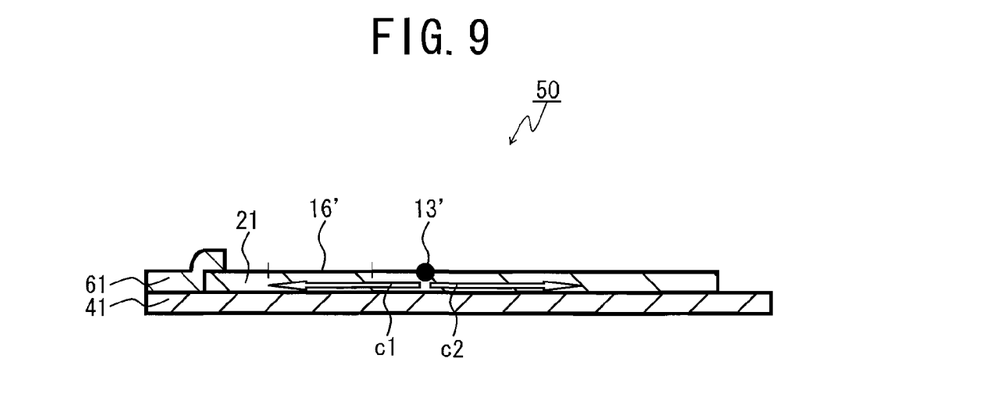
FIG. 9 is a cross-section view for explaining a flow of a specimen with respect to another example of a specimen analyzing instrument of the present invention.

On the downstream side of the specimen developing layer 21 (end of left side in FIG. 8), as shown in FIG. 9, a waste liquid absorbing pad 61 may be arranged. The waste liquid absorbing pad 61 is for collecting the waste liquid that went through the specimen analyzing portion 16', while assisting the capillary action in the specimen developing layer 21. As the waste liquid absorbing pad 61, for example, a filter paper, and the like can be used. In addition, the waste liquid absorbing pad 61 is an arbitrary component and is not necessary to be formed, but forming the pad is preferred.

The waste liquid absorbing pad 61 can be formed by fixing one end of the waste liquid absorbing pad 61 (end of left side in FIG. 9) to one end of the basal plate 41 (end of left side in FIG. 9) by using a double-sided tape or a adhesive agent, and lapping the other end of the waste liquid absorbing pad 61 (end of right side in FIG. 9) side over the end of the downstream side of the specimen developing layer 21 (end of left side in FIG. 9).

Example 2

Figure 10:
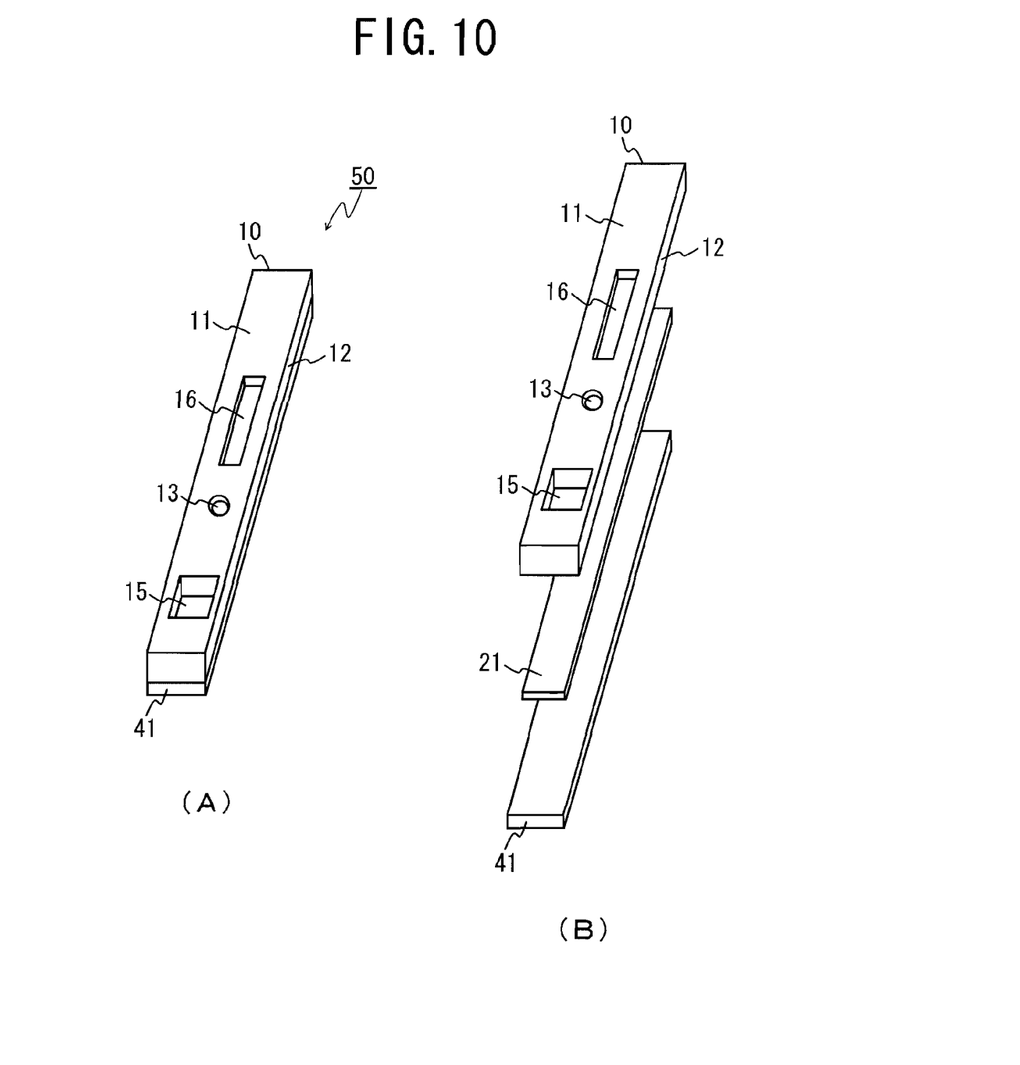
FIG. 10 is a perspective view showing a configuration of yet another example of a specimen analyzing instrument of the present invention.

FIG. 10 shows yet another example of the specimen analyzing instrument using the specimen supplying tool of the present invention. In FIG. 10, identical parts to those shown in FIG. 7 are indicated with identical numerals and symbols. As shown in FIG. 10, the configuration of this specimen analyzing instrument 50 is the same as the configuration of the specimen analyzing instrument shown in FIG. 7 except that the cover member 10 further includes a developing solvent supplying portion 15. The specimen analyzing instrument 50 of this example is used suitably for analysis of a liquid specimen using Immuno-Chromatographic Assay (ICA), for example.

Analysis of a liquid specimen using this specimen analyzing instrument 50 is explained with reference to FIG. 11. In addition, in FIG. 11, the cover member 10 is omitted as a matter of convenience.

First, a liquid specimen is introduced to the through-bore formed on the cover member. The introduced liquid specimen is supplied to a specimen supplying portion 13' of the specimen developing layer 21. In addition, the specimen supplying portion 13' is located under the through-bore formed on the cover member.

Next, a developing solvent is supplied to the developing solvent supplying portion formed on the cover member. As the developing solvent, for example, tris buffer, phosphate buffer, acetate buffer, boric buffer, and the like, can be used. In the developing solvent, a surfactant, a stabilizing agent, an antibacterial agent, and the like may be added arbitrarily. The introduced developing solvent is supplied to the developing solvent supplying portion 15' of the specimen developing layer 21. In addition, the developing solvent supplying portion 15' is located under the developing solvent supplying portion formed on the cover member.

Figure 11:
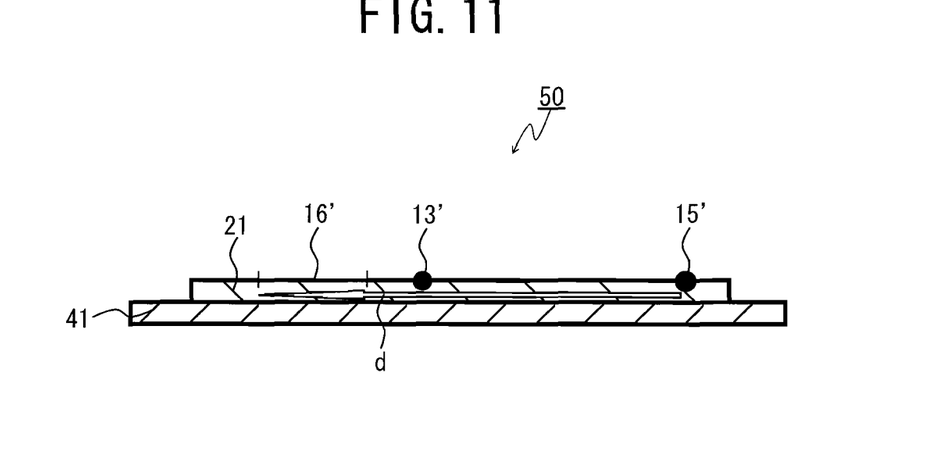
FIG. 11 is a cross-section view for explaining a flow of a specimen with respect to yet another example of a specimen analyzing instrument of the present invention.

The developing solvent supplied to the developing solvent supplying portion 15', as shown by the arrow d, develops to the downstream side of the specimen developing layer 21 (left side in FIG. 11). In this case, a liquid specimen supplied to the specimen supplying portion 13' develops in the specimen developing layer 21 by the developing solvent. Herewith, the liquid specimen reaches to a specimen analyzing portion 16' of the specimen developing layer 21. The specimen analyzing portion 16' is located under the observation port formed on the cover member.

A reagent is arranged in the specimen analyzing portion 16'. The reagent reacts with a target component to be analyzed in the liquid specimen, and a chromogenic reaction or a color change occurs. Analysis of the liquid specimen can be conducted by observing the chromogenic reaction or the color change with visual contact, or by measuring the same with an optical device such as a spectrophotometer, and the like, from the observation port formed on the cover member.

Figure 12:
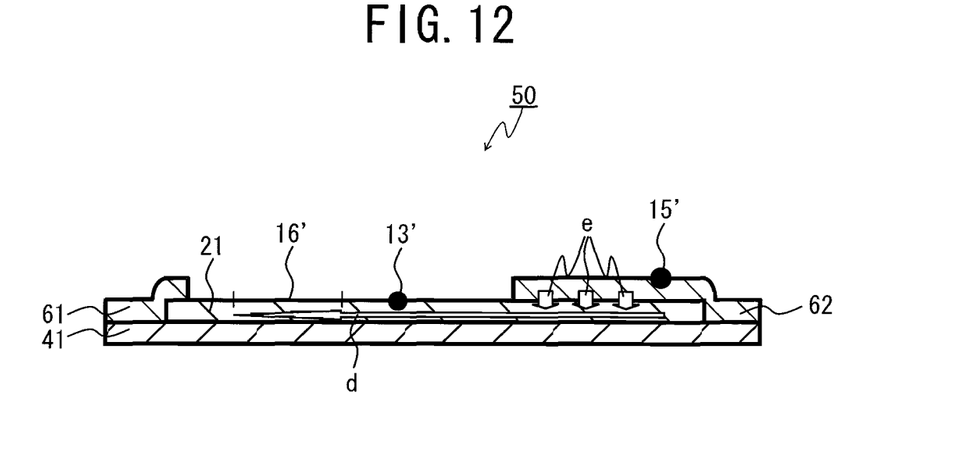
FIG. 12 is a cross-section view for explaining a flow of a specimen with respect to yet another example of a specimen analyzing instrument of the present invention.

In the upstream side (end of right side in FIG. 11) of the specimen developing layer 21, as shown in FIG. 12, a developing solvent receiving pad 62 may be provided. The developing solvent receiving pad 62 is composed of a porous material, and the formation material includes polyethylene, glass fiber, rayon, nylon, paper, cellulose, and the like. A size of the developing solvent receiving pad 62 is not particularly limited. For example, the length is in the range of 5 to 200 mm, the thickness is in the range of 0.1 to 5 mm, and the width is the same as the thickness of the specimen developing layer 21.

The developing solvent receiving pad 62 can be formed by fixing one end of the developing solvent receiving pad 62 (end of right side in FIG. 12) on one end of the basal plate 41 (end of right side in FIG. 12) by using a double-sided tape or an adhesive agent, and lapping the other end of the developing solvent receiving pad 62 (end of left side in FIG. 12) side over the specimen developing layer 21, for example. In addition, the other end of the developing solvent receiving pad 62 (end of left side in FIG. 12) side may be fixed on the specimen developing layer 21 by using a double-sided tape or an adhesive agent.

With respect to the specimen analyzing instrument 50 shown in FIG. 12, the developing solvent is supplied to the developing solvent supplying portion 15' of the developing solvent receiving pad 62. A developing solvent supplied to the developing solvent supplying portion 15', as shown in the arrow e, moves from the face where the developing solvent receiving pad 62 and the specimen developing layer 21 come in contact with each other to the specimen developing layer 21. Except for these, analysis of a liquid specimen can be conducted in the same manner as analysis of a liquid specimen using a specimen analyzing instrument shown in FIG. 11.

Waste liquid absorbing pad 61 may be arranged on the end of the downstream side of the specimen developing layer 21 (end of left side in FIG. 12). The waste liquid absorbing pad 61 is as described above.

INDUSTRIAL APPLICABILITY

With respect the specimen supplying tool of the present invention, structure is simple, and a liquid specimen and air bubbles do not remain within a through-bore for introducing a specimen. Therefore, the specimen supplying tool of the present invention and the specimen analyzing instrument using the same can be preferably used for detection, qualitative analysis, and quantitative analysis of a specific substance contained in whole blood, serum, plasma, saliva, urine, spinal fluid, and the like, and can be used in the field of clinical examinations, biochemical examinations, and the like. Further, the purposes are not limited, and these are applicable in a wide field.

The invention claimed is:

1. A specimen analyzing instrument, comprising
    a specimen supplying portion;
    a specimen analyzing portion; and
    a specimen developing layer,
    wherein:
    the specimen developing layer is configured to allow a liquid specimen to develop from an upstream side of the specimen developing layer to a downstream side of the specimen developing layer,
    the specimen supplying portion is formed on the upstream side,
    the specimen analyzing portion is formed on the downstream side, the specimen supplying portion is incorporated in a cover member of the specimen analyzing instrument by casting, the specimen supplying portion is configured to supply the liquid specimen to the specimen analyzing instrument, and the specimen supplying portion comprises:
   a substrate and
   a through-bore provided in the substrate, where the through-bore comprises a specimen inflow port and a specimen outflow port, where the specimen inflow port is one opening of the through-bore and the specimen outflow port is another opening of the through-bore, and where the specimen supplying portion further comprises a portion projecting from only part of a marginal part of the specimen outflow port provided as an extension of the specimen outflow port toward the direction of movement of the specimen and perpendicularly downwardly from a bottom portion of a lower surface of the substrate, and the specimen developing layer is arranged so that the longitudinal direction of the specimen developing layer is parallel with the lower surface of the substrate, and when the liquid specimen is introduced from the specimen inflow port to the through bore, and the introduced liquid specimen is discharged from the specimen outflow port and supplied to the specimen analyzing instrument, the liquid specimen is drawn to the projection portion, led by the projection portion, and supplied to the specimen analyzing instrument, wherein the liquid specimen moves from upstream to downstream in the specimen analyzing instrument, the projection portion is formed on the upstream side of the marginal part of the specimen outflow port, and the projection portion is not formed on the downstream side of the marginal part of the specimen outflow port, and wherein the upstream side of the specimen developing layer is at one of the specimen developing layer in the longitudinal direction and the downstream side of the specimen developing layer is at the other end of the specimen developing layer in the longitudinal direction.

2. The specimen analyzing instrument according to claim 1, wherein a bore diameter of the specimen inflow port is longer than a bore diameter of the specimen outflow port.

3. The specimen analyzing instrument according to claim 1, further comprising a developing solvent supplying portion on the specimen developing layer upstream side relative to the specimen supplying portion, wherein the liquid specimen develops in the specimen developing layer by a developing solvent supplied from the developing solvent supplying portion.

4. The specimen analyzing instrument according to claim 1, further comprising an observation port configured to observe the specimen analyzing portion from outside.

* * * * *